United States Patent
Wissel et al.

(10) Patent No.: US 11,819,362 B2
(45) Date of Patent: Nov. 21, 2023

(54) REAL TIME ULTRASOUND IMAGING METHOD AND SYSTEM USING AN ADAPTED 3D MODEL TO PERFORM PROCESSING TO GENERATE AND DISPLAY HIGHER RESOLUTION ULTRASOUND IMAGE DATA

(71) Applicant: KONINKLIJKE PHILIPS N.V., Eindhoven (NL)

(72) Inventors: Tobias Wissel, Lübeck (DE); Frank Michael Weber, Hamburg (DE); Arne Ewald, Hamburg (DE); Irina Waechter-Stehle, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 449 days.

(21) Appl. No.: 16/622,662

(22) PCT Filed: Jun. 19, 2018

(86) PCT No.: PCT/EP2018/066163
§ 371 (c)(1),
(2) Date: Dec. 13, 2019

(87) PCT Pub. No.: WO2019/002006
PCT Pub. Date: Jan. 3, 2019

(65) Prior Publication Data
US 2020/0205784 A1     Jul. 2, 2020

(30) Foreign Application Priority Data

Jun. 26, 2017   (EP) ..................... 17177771

(51) Int. Cl.
*A61B 8/08*     (2006.01)
*A61B 8/14*     (2006.01)
(Continued)

(52) U.S. Cl.
CPC ............ *A61B 8/483* (2013.01); *A61B 8/0883* (2013.01); *A61B 8/145* (2013.01); *A61B 8/4488* (2013.01); *A61B 8/463* (2013.01); *A61B 8/5253* (2013.01)

(58) Field of Classification Search
CPC ....... A61B 8/483; A61B 8/0883; A61B 8/145; A61B 8/4488; A61B 8/463; A61B 8/5253;
(Continued)

(56) References Cited

U.S. PATENT DOCUMENTS

| 5,682,895 A | 11/1997 | Ishiguro |
| 2010/0292574 A1* | 11/2010 | Hyun ..................... A61B 8/463 600/443 |

(Continued)

FOREIGN PATENT DOCUMENTS

| JP | 2005073817 A | 3/2005 |
| JP | 2005095328 A | 4/2005 |

(Continued)

OTHER PUBLICATIONS

Ploquin, et al., "Resolution enhancement in medical ultrasound imaging", Journal of Medical Imaging, Jan.-Mar. 2015, vol. 2(1), pp. 017001-1 to 017001-12. (Year: 2015).*

(Continued)

*Primary Examiner* — Christopher Koharski
*Assistant Examiner* — Richmond J Van Winter

(57) ABSTRACT

A method is provided for generating an ultrasound image of an anatomical region having a volume. First image low resolution image data is enhanced by adapting a 3D anatomical model to the image data to generate a second, greater, quantity of ultrasound image data in respect of the anatomical region. The enhanced volumetric information is then displayed. An anatomical model is thus used to com- (Continued)

plete partial image data thereby increasing the image resolution, so that a high resolution volumetric image can be displayed with a reduced image capture time.

8 Claims, 3 Drawing Sheets

(51) Int. Cl.
*A61B 8/00* (2006.01)
*G01S 15/89* (2006.01)
*G01S 7/52* (2006.01)
*G06T 19/20* (2011.01)

(58) Field of Classification Search
CPC ... A61B 8/466; A61B 8/5246; G01S 15/8915; G01S 15/8977; G01S 7/5208; G01S 15/8925; G01S 15/8993; G06T 2210/41; G06T 2219/2021; G06T 19/20
See application file for complete search history.

(56) References Cited

U.S. PATENT DOCUMENTS

| 2012/0053464 | A1* | 3/2012 | Murashita | A61B 8/483 600/443 |
| 2012/0083695 | A1* | 4/2012 | Napolitano | G10K 11/341 600/443 |
| 2012/0253170 | A1 | 10/2012 | Kim et al. | |
| 2013/0066206 | A1 | 3/2013 | Prater et al. | |
| 2013/0066207 | A1 | 3/2013 | Prater et al. | |
| 2015/0018698 | A1 | 1/2015 | Safran et al. | |
| 2016/0113632 | A1 | 4/2016 | Ribes et al. | |
| 2018/0344290 | A1* | 12/2018 | Veronesi | G06T 7/00 |
| 2019/0142392 | A1* | 5/2019 | Carolus | A61B 8/5246 600/437 |

FOREIGN PATENT DOCUMENTS

| WO | WO-0120552 A1 * | 3/2001 | A61B 34/20 |
| WO | 2007034425 A2 | 3/2007 | |
| WO | 2014080319 A1 | 5/2014 | |
| WO | WO-2014080319 A1 * | 5/2014 | A61B 8/0866 |
| WO | 2017042304 A1 | 3/2017 | |

OTHER PUBLICATIONS

Alessandrini, et al., "A Pipeline for the Generation of Realistic 3D Synthetic Echocardiographic Sequences: Methodology and Open-Access Database", IEEE Transactions on Medical Imaging, vol. 34, No. 7, Jul. 2015, pp. 1436-1451. (Year: 2015).*
Demirli, et al., "Model Based Restoration of the RF Data for High Resolution Vascular Ultrasound Imaging", 2013 Joint UFFC, ETFT and PFM Symposium, pp. 895-898.
Ploquin, et al., "Resolution enhancement in medical ultrasound imaging", Journal of Medical Imaging, Jan.-Mar. 2015, vol. 2(1), pp. 017001-1 to 017001-12.
Ecabert, et al., "Automatic Model-Based Segmentation of the Heart in CT Images", IEEE Transactions on Medical Imaging, vol. 27, No. 9, Sep. 2008, pp. 1189-1201.
Alessandrini, et al., "A Pipeline for the Generation of Realistic 3D Synthetic Echocardiographic Sequences: Methodology and Open-Access Database", IEEE Transactions on Medical Imaging, vol. 34, No. 7, Jul. 2015, pp. 1436-1451.
International Search Report and Written Opinion for International Application No. PCT/EP2018/066163, filed Jun. 19, 2018, 16 pages.

* cited by examiner

REAL TIME ULTRASOUND IMAGING METHOD AND SYSTEM USING AN ADAPTED 3D MODEL TO PERFORM PROCESSING TO GENERATE AND DISPLAY HIGHER RESOLUTION ULTRASOUND IMAGE DATA

RELATED APPLICATIONS

This application is the U.S. National Phase application under 35 U.S.C. § 371 of International Application No. PCT/EP2018/066163, filed on Jun. 19, 2018, which claims priority to and the of European Application No. 17177771.7, filed Jun. 26, 2017. These applications are hereby incorporated in their entirety by reference herein.

FIELD OF THE INVENTION

This invention relates to an ultrasound imaging method and apparatus

BACKGROUND OF THE INVENTION

Ultrasound imaging is increasingly being employed in a variety of different applications. It is important that the image produced by the ultrasound system is as clear and accurate as possible so as to give the user a realistic interpretation of the subject being scanned. This is especially the case when the subject in question is a patient undergoing a medical ultrasound scan. In this situation, the ability of a physician to make an accurate diagnosis is dependent on the quality of the image produced by the ultrasound system.

Due to its excellent temporal resolution and its non-invasiveness, ultrasound plays an important role in cardiovascular imaging. Most commonly, Transthoracic Echo (TTE) imaging is used to determine left ventricular quantities such as volume or ejection fraction. To minimize manual effort and user variability, this process has been automated by employing anatomically intelligent model-based segmentation (Ecabert, O. et al.; IEEE Transactions on, 2008, 27, pp. 1189-1201).

The diagnostic value of acquiring 3D scans over time strongly depends on the sampling rate. The latter is mainly restricted by the amount of volume data acquired for one scan.

There is thus a compromise between the speed of recording and the quality of an acquired image. However, in order to sufficiently capture and judge diagnostically relevant motion as well as abnormalities thereof, high frame rates are sometimes necessary. Therefore, certain clinical applications still entail the need for faster recordings than with a full 3D scan and sacrifice possibly valuable 3D volume information by restricting the field of view.

There is therefore a need for a method and system which enables high resolution image data to be acquired in a reduced time period. Thus, the invention aims to resolve the dilemma that both, high speed and large volume acquisition, cannot be achieved simultaneously.

WO 2017/042304 discloses an ultrasound system in which ultrasound beams of variable frequency are generated, with a higher frequency used when imaging within a region of interest than when imaging outside the region of interest. Thus, a wider field of view and higher penetration depth is used outside the region of interest, and within the region of interest a higher resolution image is obtained.

SUMMARY OF THE INVENTION

The invention is defined by the claims.

In accordance with an aspect, there is provided a real time imaging method for generating an ultrasound image of an anatomical region having a volume, the method comprising:
 receiving image data for the anatomical region in the form of a first quantity of ultrasound image data in respect of the anatomical region volume;
 accessing a 3D model which is a representation of the anatomical region and which defines the spatial extent of anatomy parts of the anatomical region;
 adapting the 3D model to the image data; and
 using the adapted 3D model to perform processing of the image data thereby to generate a second, greater, quantity of ultrasound image data in respect of the anatomical region; and
 displaying volumetric information using the second quantity of ultrasound image data.

This method makes use of an anatomical model to complete partial image data thereby increasing the image resolution, so that a high resolution volumetric image can be displayed with a reduced image capture time. This enables real time imaging so that spatio-temporal motion patterns may be detected, which may be specific to a particular patient, disease or pathology. For example, this may be of particular interest for valvular heart disease diagnosis and treatment planning.

The term "adapting" is thus used to relate to fitting the anatomical model to the received image data, which may be coarse (spatially or temporally) image data. The term "processing of the image data" is used to refer to the conversion of the received (e.g. coarse) image data into higher resolution data (with higher spatial or temporal resolution), using information from the adapted 3D model i.e. taking anatomical information into account.

The 3D model may be a generic representation of the anatomical region, either for any subject, or tailored to a particular class of patients (e.g. by age, gender, size or medical condition).

The 3D model representation is for example a triangular mesh and the ultrasound image comprises a set of voxels, and both are in 3D space. The model can thus be deformed to fit the low resolution image. This is termed a model adaptation.

The mesh model is created based on a training population. The destination resolution (of the second quantity of ultrasound data) can be defined by the user. Typical clinical resolutions are of 0.3-1.0 mm voxel edge length. By lowering the image capture resolution or dropping certain parts of the data, a higher capture rate is achieved. By using an anatomically intelligent volume completion (i.e. the processing of the image data), the data still has the desired clinical resolution at the visualization stage afterwards.

Adapting the 3D model to the image data may comprise:
 from the image data, generating modified image data, without reference to the 3D model; and
 adapting the 3D model to the modified image data.

To create this modified image data, certain voxels can be filled with the recorded imaging information. Gaps between these voxels which originate from the sparse way of data acquisition may be filled using simple (by which is meant non-anatomically intelligent) interpolation (such as nearest neighbor or trilinear interpolation).

The processing of the image data before any use of the anatomical model will be termed "modification". Such processing makes no use of any extracted anatomical information. This modification thus does not involve any delineation of regions of different characteristic anatomical or ultrasound properties.

The resulting modified image data may have steps and may be coarse still when looking at the image information, but model adaptation (i.e. fitting) is still possible. The image data modification (which may be a non-anatomically intelligent interpolation) is only used for the purpose of the adaptation step, by which the volume data is fitted to the anatomical model.

The image data may comprise a set of 2D slice images, and the second quantity of ultrasound image data comprises a 3D volumetric image with additional image data between the 2D slice images.

Alternatively, the image data may comprise a 3D volumetric image of a first resolution, and wherein the second quantity of ultrasound image data defines a 3D volumetric image of a greater, second resolution.

The method produces high resolution 3D image data either by providing additional data between 2D slices or by providing additional data to the lower resolution 3D image data.

These two cases result from the way data is acquired. Data is typically acquired in polar coordinates and is then interpolated to Cartesian coordinates either resulting in a (e.g. low) resolution image volume or a set of slices in this new Cartesian space. The model is then adapted either to this data directly or to a modified image (which results from the non-anatomically intelligent interpolation explained above) based on the known data. After the model is adapted and therefore anatomical regions/segments are defined, then the anatomically intelligent image processing is performed to complete the image data.

The low resolution image data is for example obtained on the basis that parts of the scan lines of a complete full volume are omitted (e.g. in a checker-board fashion). The physical beam width may be the same as would be used for a full resolution image. Thus, the low resolution image for example may have the same beam width and same focus as for a high resolution image.

There may for example be 3 to 10 image slices in each of two orthogonal directions if the low resolution data is a subset of slices. The low resolution image may for example comprise 25% or 50% of the scan lines if the low resolution data is based on partial scan lines.

The ultrasound system may be used in a low resolution mode when it has the capability of higher resolution, for the purposes of speeding up image acquisition. Alternatively, a lower cost ultrasound system may be used at its full resolution so that the system cost is kept down for a system able to deliver high resolution images.

The adapting the 3D model to the image data may comprise identifying anatomical boundaries between different regions, and wherein the processing of the image data comprises processing data of the first quantity of ultrasound image data within the different regions.

The processing of the image data (i.e. the data volume completion) may thus be performed within anatomical regions, but not across boundaries (transitions) between those regions, so that the boundaries can remain and maintain their distinct properties which are linked to their anatomical meaning. A region may also share information relating to the broader (anatomical) context, which can for example be use to assist image data processing between the different regions i.e. in the transitions.

The identification of regions by the adapting step may be termed "segmentation". The regions could be distinct anatomical regions e.g. myocardium muscle tissue, but also conjunctions between two anatomical regions/tissues. Regions are defined as areas having distinct properties in terms of ultrasound imaging.

Thus, similar anatomical regions are taken into account (e.g. for the image data processing, in respect of the myocardium only those voxels known to be in the myocardium are used, in respect of a blood pool only those voxels known to be in the blood pool are used, in respect of a conjunction between muscle and blood pool only those voxels also lying on such a conjunction are used, etc.). By defining anatomical regions based on the segmentation of the adapting step, restrictions are imposed on the data processing such that there is anatomically intelligent volume completion.

The data processing thus has a spatial constraint (only using information in the neighborhood of the voxel of interest) and an anatomical constraint (using information for voxels having an anatomical meaning similar to the voxel of interest).

The processing of the image data within the different regions may comprise:
nearest neighbor interpolation;
linear interpolation; or
non-linear interpolation.

These different interpolation methods may be used to create the additional image data, but within identified regions.

The processing of the image data within the regions may instead comprise:
interpolation based on ultrasound signal statistics in the spatial or anatomical neighborhood.

A statistical analysis provides an approach which models the ultrasound signal magnitude of a voxel with the most likely value from a probability distribution having certain learned parameters. Finally, the set of probability distributions enables an interpolation model that is used together with the model-based segmentation output to fill the missing gaps to create the higher resolution image.

The processing of the image data may comprise determining the location and characteristics of point scatterers and a convolution with a point spread function.

This approach for example involves randomly defining a set of point scatterers across the ultrasound volume then convolving the resulting scatter map with a 3D spatially varying point spread function (PSF). The PSF appearance and variance is defined by the ultrasound imaging parameters as well as the transducer.

The invention also provides a computer program comprising computer program code means which is adapted, when said computer program is run on a computer, to implement the method as defined above.

The invention also provides a processor arrangement for controlling the generation of a real time ultrasound image of an anatomical region having a volume, wherein the processor arrangement is adapted to:
receive image data for the anatomical region in the form of a first quantity of ultrasound image data in respect of the anatomical region volume;
access a 3D model which is a representation of the anatomical region and which defines the spatial extent of anatomy parts of the anatomical region; and
adapt the 3D model to the image data;
use the adapted 3D model to perform processing of the image data thereby to generate a second, greater, quantity of ultrasound image data in respect of the anatomical region; and display volumetric information using the second quantity of ultrasound image data.

This processor implements the method described above.

The processor may be adapted to adapt the 3D model to the image data by:

from the image data, generating modified image data, without reference to the 3D model; and fitting the 3D model to the modified image data.

As explained above, the processor may be adapted to adapt the 3D model to the image data by identifying anatomical boundaries between different regions and perform processing of the image data of the first quantity of ultrasound image data within the different regions. Processing of the image data within the different regions may then be made using: nearest neighbor interpolation; linear interpolation; non-linear interpolation; interpolation based on ultrasound signal statistics in the spatial or anatomical neighborhood; or determination of the location and characteristics of point scatterers and a convolution with a point spread function.

The invention also provides an ultrasound system for generating a real time ultrasound image of an anatomical region having a volume, comprising:

an ultrasonic transducer array, wherein the ultrasonic transducer array is capable of emitting and receiving ultrasonic signals which provide a first quantity of ultrasound image data in respect of the anatomical region volume;

a database which stores a 3D model which is a representation of the anatomical region and which defines the spatial extent of anatomy parts of the anatomical region;

a processor as defined above; and a display for displaying volumetric information using the second quantity of ultrasound image data.

A user interface may be provided which allows a user to set an image sampling speed.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
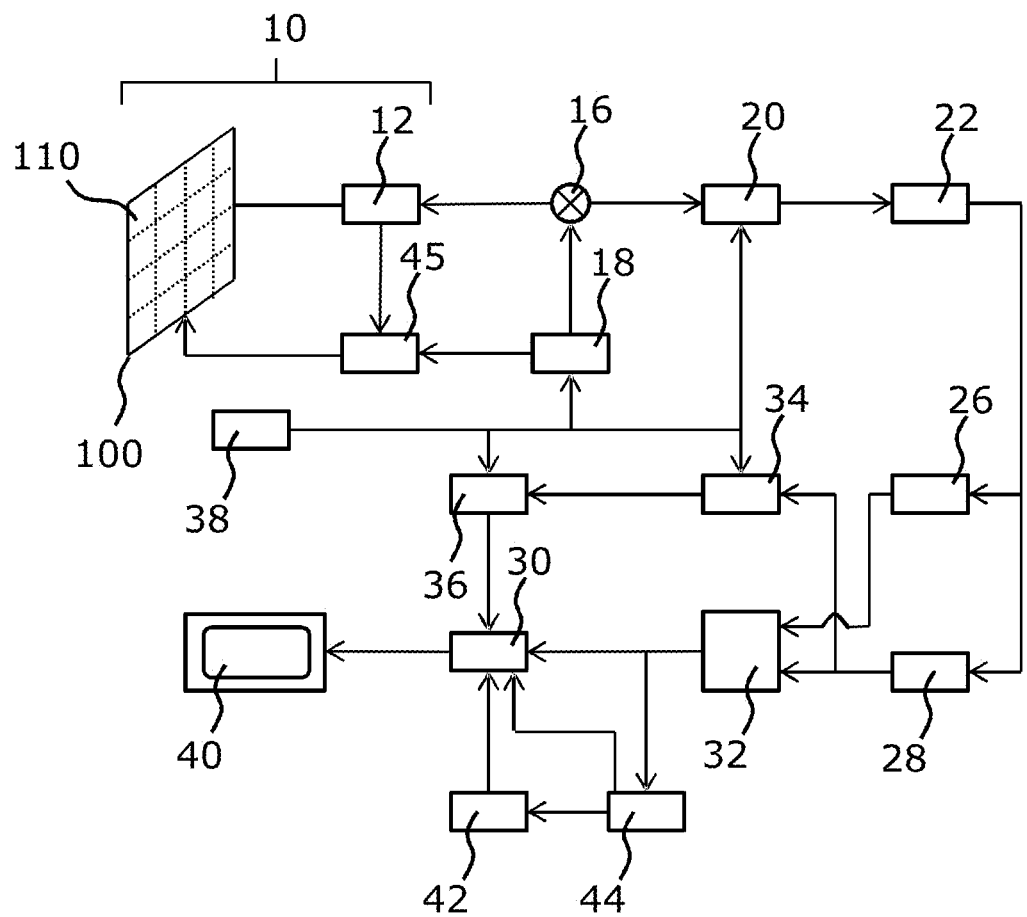
FIG. 1 shows an ultrasound diagnostic imaging system to explain the general operation.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

Provided is a method for generating an ultrasound image of an anatomical region having a volume. First image low resolution image data is enhanced by adapting a 3D anatomical model to the image data to generate a second, greater, quantity of ultrasound image data in respect of the anatomical region. The enhanced volumetric information is then displayed. An anatomical model is thus used to complete partial image data thereby increasing the image resolution, so that a high resolution volumetric image can be displayed with a reduced image capture time.

This invention aims at improving the compromise between image acquisition speed and image quality. By sparsely sampling only selected view planes or scan lines instead of recording the entire volume, the acquisition time may be reduced. Anatomically intelligent model-based segmentation can then delineate relevant anatomical structures by fitting a 3D model to the data. Together with the echo information from the sampled subset, this 3D model of the region (e.g. organ) of interest can be used to approximate and finally render a full 3D ultrasound volume for each point in time.

Concretely, the 3D model contributes as a boundary condition for the anatomical context and enriches a purely intensity-driven data completion e.g. by providing information about the expected type of tissue at a certain location and possibly its properties. This information can be used in different ways and yields more realistic, but also case-specific results.

Overall, anatomically intelligent 3D volume completion provides a way to estimate a full 3D dataset with higher acquisition speed than for a full 3D scan. It constitutes an option of 3D visualization, while still providing enough temporal resolution to identify anatomical effects relevant for diagnosis.

The general operation of an exemplary ultrasound diagnostic imaging system will first be described, with reference to FIG. 1.

The system comprises an array transducer probe 10 which has a CMUT transducer array 100 for transmitting ultrasound waves and receiving echo information. The transducer array 100 may alternatively comprise piezoelectric transducers formed of materials such as PZT or PVDF. The transducer array 100 is a two-dimensional array of transducers 110 capable of scanning in a 2D plane or in three dimensions for 3D imaging. In another example, the transducer array 100 may be a 1D array.

The transducer array 100 is coupled to a microbeamformer 12 in the probe which controls reception of signals by the CMUT array cells or piezoelectric elements. Microbeamformers are capable of at least partial beamforming of the signals received by sub-arrays (or "groups" or "patches") of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 12 is coupled by the probe cable to a transmit/receive (T/R) switch 16 which switches between transmission and reception and protects the main beamformer 20 from high energy transmit signals when a microbeamformer is not used and the transducer array 100 is operated directly by the main system beamformer. The transmission of ultrasound beams from the transducer array 100 is directed by a transducer controller 18 coupled to the microbeamformer by the T/R switch 16 and a main transmission beamformer (not shown), which receives input from the user's operation of the user interface or control panel 38.

One of the functions controlled by the transducer controller 18 is the direction in which beams are steered and focused. Beams may be steered straight ahead from (orthogonal to) the transducer array 100, or at different angles for a wider field of view. The transducer controller 18 can be coupled to control a DC bias control 45 for the CMUT array. The DC bias control 45 sets DC bias voltage(s) that are applied to the CMUT cells.

In the reception channel, partially beamformed signals are produced by the microbeamformer 12 and are coupled to a main receive beamformer 20 where the partially beamformed signals from individual patches of transducers are combined into a fully beamformed signal. For example, the main beamformer 20 may have 128 channels, each of which receives a partially beamformed signal from a patch of dozens or hundreds of CMUT transducer cells or piezoelectric elements. In this way the signals received by thousands of transducers of a transducer array 100 can contribute efficiently to a single beamformed signal.

The beamformed reception signals are coupled to a signal processor 22. The signal processor 22 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and microbubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 100 which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 26 and a Doppler processor 28. The B mode processor 26 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor 28 typically includes a wall filter with parameters which may be set to pass and/or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on a display device 40. In addition to being used for imaging, the blood flow values produced by the Doppler processor 28 and tissue structure information produced by the B mode processor 26 are coupled to a quantification processor 34. The quantification processor 34 produces measures of different flow conditions such as the volume rate of blood flow as well as structural measurements such as the sizes of organs and gestational age. The quantification processor 34 may receive input from the user control panel 38, such as the point in the anatomy of an image where a measurement is to be made. Output data from the quantification processor 34 is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface 38 is also coupled to the transmit controller 18 to control the generation of ultrasound signals from the transducer array 100 and hence the images produced by the transducer array 100 and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface 38 is also coupled to the multi-planar reformatter 44 for selection and control of the planes of multiple multi-planar reformatted (MPR) images which may be used to perform quantified measures in the image field of the MPR images.

A processor arrangement may be adapted to perform any part of the method described below (with reference to FIG.

4). The processor arrangement may, for instance, be included in one or more of the previously described processors, such as the controller 18, the quantification processor 34 and the graphics processor 36. Alternatively, the processor arrangement may be an additional module.

In an embodiment, the method described below may be implemented by a computer program code, included in a computer program product, which is run on a computer.

Known ultrasound probes are technically capable of recording only certain planes of the entire volume. A matrix array probe, for instance, can sample only pre-defined vertical or horizontal planes or even only segments of these planes. Thus, given a minimally required sampling speed, the amount of sampled volume information could therefore be adjusted to be able to meet this speed.

Figure 2:
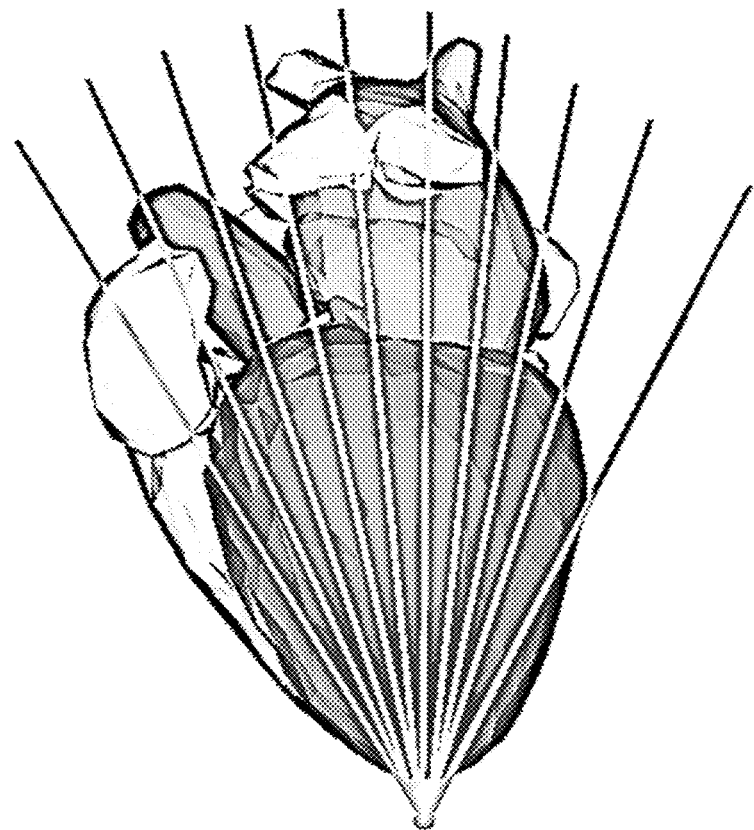
FIG. 2 shows 2D image slice locations through the heart.

FIG. 2 illustrates this idea by showing a fan like arrangement of planar views, instead of the entire volume. By activating only certain elements of a matrix probe, the ultrasound acquisition can be restricted to multiple planar views instead of the entire volume. A 3D anatomically intelligent model is then fitted in accordance with the invention to the data and finally used to approximate the empty gaps.

Figure 3:
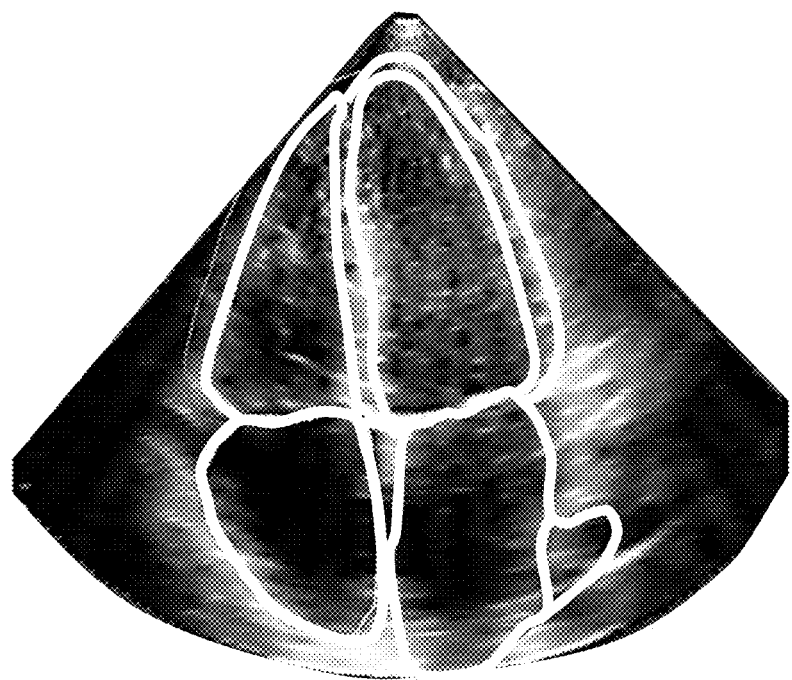
FIG. 3 shows one 2D image of the slices of FIG. 2.

FIG. 3 shows a four chamber view as an example plane with the surfaces of the 3D model cutting through the contours of the relevant anatomical boundaries. The view thus enables segmentation of the image into distinct anatomical regions.

Figure 4:
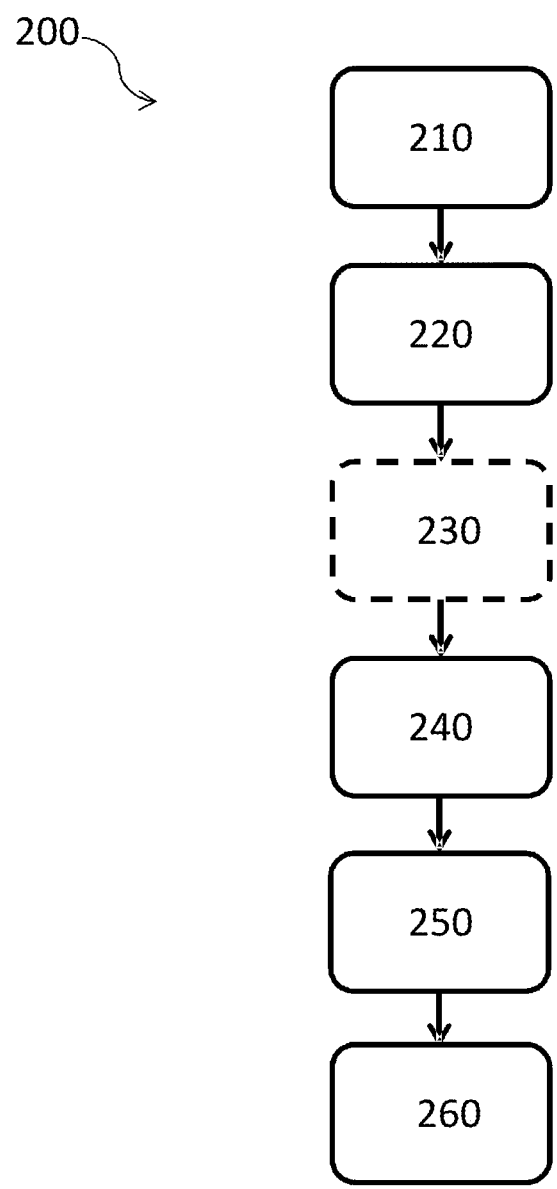
FIG. 4 shows an ultrasound imaging method.

FIG. 4 shows a method 200 for generating an ultrasound image of an anatomical region having a volume, for example as shown in FIG. 2.

In step 210 image data is received for the anatomical region in the form of a first quantity of ultrasound image data in respect of the anatomical region volume. This first quantity of data corresponds to a low resolution or coarse image. It may comprise a set of 2D slice images or a 3D volumetric image. Typical clinical resolutions are of 0.3-1.0 mm voxel edge length. By lowering the image capture resolution so that lower resolution data is obtained, or dropping certain parts of the data, a higher capture rate is achieved. The low resolution image is for example based on selectively sampling a subset of the volumetric object, e.g. a set of planar views. Alternatively, the complete field of view of the 3D volume may be sampled but with a reduced density of scan lines, e.g. only every other available beam in each dimension. This for example yields a checker-board pattern. The physical beam width may in that case be the same as would be used for a full resolution image. There may for example be 3 to 10 image slices in each of two orthogonal directions if the low resolution data is a subset of slices. The low resolution image may for example comprise 25% or 50% of the scan lines.

In step 220 a 3D model is accessed which is a representation of the anatomical region. The 3D model may be a generic representation of the anatomical region (e.g. the heart), either for any subject, or tailored to a particular class of patients (e.g. by age, gender, size or medical condition). The 3D model representation is for example a triangular mesh. The mesh model is for example created based on a training population. The 3D model defines the spatial extent of the respective anatomy parts. Each triangle has associated information which is trained in a data-driven way. This information provides identification in respect of that triangle of how a typical, desired neighborhood would appear in an ultrasound image.

In step 240, the 3D model is adapted to the image data. This involves fitting the anatomical model to the coarse image data.

The adaptation makes use of an anatomically intelligent segmentation algorithm which adapts the model representation of the region (e.g. organ) of interest to the coarsely sampled data or an already naively interpolated version of it (for example with interpolation between the sparsely sampled scanlines). The latter example involves first generating modified image data as shown in optional step 230, without reference to the 3D model and then adapting the 3D model to the modified image data. To create this modified image data, certain voxels can be filled with the recorded imaging information. Gaps between these voxels which originate from the sparse way of data acquisition may be filled using simple interpolation (such as nearest neighbor or linear interpolation). This image modification is before any use of the anatomical model.

This process of delineating relevant anatomical structures using automated by model-based segmentation approaches is known to those skilled in the art and is for example disclosed in Ecabert, O.; Peters, J.; Schramm, H.; Lorenz, C.; von Berg, J.; Walker, M.; Vembar, M.; Olszewski, M.; Subramanyan, K.; Lavi, G. & Weese, J. Automatic Model-Based Segmentation of the Heart in CT Images Medical Imaging, IEEE Transactions on, 2008, 27, pp. 1189-1201.

In brief, the model-based segmentation involves localizing the region of interest, e.g. the heart, in the image. Localization may be achieved via a completely automatic method, e.g. using a generalized Hough Transform (GHT). In such a technique, the center of gravity of the initial triangle mesh model is placed into a 3D image according to an optimal position obtained by a GHT. The initial mesh model is thus translated and scaled so as to be positioned in the image. Alternatively or additionally, other localization techniques such as 'Hough forests' and classification approaches may be used.

Following localization, the segmentation routine is implemented in order to adapt the model to the organ boundaries. The segmentation routine may be a model-based segmentation routine which may be carried out in multiple steps, leading from a very coarse to a finer adaption. In such a routine, the initial mesh may be adapted rigidly by scaling, shifting and rotating the whole mesh using a global similarity transformation. This may be followed by a global affine transformation to allow for squeezing or stretching of the model data and a multi affine transformation which adapts anatomical regions such as ventricles and atria individually. The mesh resulting from previous adaptation iterations may then be adapted in a deformable fashion, i.e. each triangle of the mesh is allowed to move independently.

The model adaptation is thus an iterative optimization, where all triangles collectively strive to approach locations in the given image data for the ultrasound volume that come close to their stored information. In this way, a generic anatomical mesh is deformed and adapted to the given image.

The output is for example a surface-based description of the organ. In essence, the adaptation involves deforming the model to fit the low resolution (or modified low resolution) image. In this way, anatomical boundaries between different regions are identified.

In step 250, the adapted 3D model is used to perform processing of the image data thereby to generate a second, greater, quantity of ultrasound image data in respect of the anatomical region. This "processing of the image data" provides conversion of the coarse image data into higher resolution data, using information from the adapted 3D model i.e. taking anatomical information into account. By using an anatomically intelligent volume completion, the data still has the desired clinical resolution at the visualization stage afterwards. The desired destination resolution can for example be defined by the user by means of a user interface.

The processing of the image data is performed such that the anatomical regions are taken into account. In particular, the ultrasound image data is processed region by region, rather than across boundaries between those regions, so that the boundaries can remain and maintain their distinct properties which are linked to their anatomical meaning. In this way, by defining anatomical regions based on the segmentation of the adapting step 240, restrictions are imposed on the data processing such that there is anatomically intelligent volume completion (where "volume completion" refers to the step of increasing the resolution).

The processing of the image data within the different regions may comprise:
  nearest neighbor interpolation;
  linear interpolation (e.g. trilinear interpolation in 3D volume space); or
  non-linear interpolation.

These different interpolation methods may be used to create the additional image data, but within identified regions. Thus, the interpolation is carried out locally using the anatomical boundaries. For example, for missing data in the left ventricular myocardium, an intensity is derived only from those neighbor values which are also located in the left ventricular myocardium.

An identified region may also share information with other regions, for example including information about the broader (anatomical) context. This could support interpolation for example by providing information about how far away is the next (and which) region. This for example reduces the total number of regions needed, since it would reduce the number of transition regions that need to be defined. Thus, transitions between regions could be made smoother by providing additional information in the main anatomical regions.

Along similar lines, local statistics can be derived for the neighborhood of each of the missing volume parts. The statistics are estimated from the available data and constitute a local data generating distribution. From this distribution sampled data is used to fill in the missing parts in spatial proximity. Interpolation may additionally exploit prior information encoded in the model, for example the model could include information about typical regional properties of the tissue.

An interpolation may be based on ultrasound signal statistics in the spatial or anatomical neighborhood. A statistical analysis provides an approach which models the ultrasound signal magnitude of a voxel with the most likely value from a probability distribution having certain learned parameters (e.g. a Gaussian distribution with mean and variance). These parameters can be estimated in a data-driven way from examples, stored in an offline database, or from the recorded or known image data of the current volume. The distribution can be such that there is one distribution per anatomical sub-region, which again exploits the knowledge from the segmentation.

Also, neighborhood information (optionally also restricted to similar anatomical regions) can be taken into account by introducing a spatial covariance between voxels, for example using a Gaussian process.

Finally, the set of probability distributions enables an interpolation model that is used together with the model-based segmentation output to fill the missing gaps to create the higher resolution image.

Thus various conventional interpolation approaches may be used.

In another approach, the processing of the image data (to increase the resolution) may comprise determining the location and characteristics of point scatterers and a convolution with a point spread function.

This approach is disclosed as a way of simulating ultrasound images in Alessandrini, M.; Craene, M. D.; Bernard, O.; Giffard-Roisin, S.; Allain, P.; Waechter-Stehle, I.; Weese, J.; Saloux, E.; Delingette, H.; Sermesant, M. & D'hooge, J. A Pipeline for the Generation of Realistic 3D Synthetic Echocardiographic Sequences: Methodology and Open-Access Database IEEE Transactions on Medical Imaging, 2015, 34, 1436-1451. While the locations of the point scatterers can be obtained from the boundaries of the adapted 3D model, their properties can be derived from the sparsely acquired, surrounding image intensities or/and from information about tissue type or mechanical properties which has been attached to the model as additional prior knowledge.

This approach is based on randomly defining a set of point scatterers across the ultrasound volume then convolving the resulting scatter map with a 3D spatially varying point spread function (PSF). The PSF appearance and variance is defined by the ultrasound imaging parameters as well as the transducer. Different local signals in the ultrasound image (e.g. myocardium versus blood pool) are distinguished by their echogenicity.

This echogenicity can be simulated by either manipulating the density of scatterers or by manipulating the amplitudes assigned to each scatterer. How, where and to which extent this manipulation is done in the ultrasound volume depends on the anatomical labels for that location. This information is derived from the model-based segmentation and a database of typical templates. The low resolution image itself may function as the reference, since parts of the image are known. The latter information then defines the typical amplitude distribution/magnitude for a particular anatomical region.

In step 260, the volumetric information is displayed using the second quantity of ultrasound image data, i.e. the higher resolution image data.

The image is displayed over time and this allows user interaction to examine and diagnose the given case.

The overall method thus enables sparsely sampled data to give a higher resolution approximation of a volume for display to the user, as a replacement of the incompletely acquired data. The approximation of signals in unknown sub-volumes is supported by neighboring intensities of the recorded samples. However, prior knowledge about the typical appearances of the imaged organ are used to provide a better estimate or to possibly to reduce further the amount of data needed.

The invention can be used in applications where high sampling rates are required to detect relevant spatio-temporal patterns of motion which are then characteristic for a certain patient, pathology or disease. An example is given of valvular heart disease where dynamic aspects which can be acquired non-invasively and without ionizing radiation are highly relevant for diagnosis and treatment planning.

The optimal sampling speed can be set by the user or based on a recommendation for the given application. It defines the extent of sparse sampling which is necessary to meet this requirement. After recording the sparse data, the approximated volume is visualized and made available to the user for interaction.

The invention is not restricted to the heart, but can be applied for other segmentation problems as well.

As discussed above, embodiments make use of a processor arrangement for performing the data processing steps. The processor may be implemented by the signal processor 22 of the system of FIG. 1. The processor arrangement can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A real time imaging method for generating an ultrasound image of a plurality of different anatomical regions within a volume, the method comprising:
   receiving low resolution image data for the anatomical regions in the form of a first quantity of ultrasound image data in respect of the anatomical regions within the volume;
   accessing a 3D model which is a representation of the anatomical regions and which defines the spatial extent of anatomy of the anatomical regions by boundaries;
   adapting the 3D model to the low resolution image data; and
   using the adapted 3D model to perform processing of the image data within each region and avoid processing together image data of different regions separated by a boundary thereby to generate a second, greater, quantity of ultrasound image data of higher resolution in respect of the anatomical regions; and
   displaying volumetric information using the second quantity of ultrasound image data at a resolution higher than that of the low resolution.

2. A method as claimed in claim 1, wherein adapting the 3D model to the image data comprises:
   from the image data, generating modified image data, without reference to the 3D model; and
   adapting the 3D model to the modified image data.

3. A method as claimed in claim 1, wherein:
   the image data comprises a set of 2D slice images, and the second quantity of ultrasound image data comprises a 3D volumetric image with additional image data between the 2D slice images; or
   the image data comprises a 3D volumetric image of a first resolution, and wherein the second quantity of ultrasound image data defines a 3D volumetric image of a greater, second resolution.

4. A method as claimed in claim 1, wherein the adapting the 3D model to the image data comprises identifying anatomical boundaries between the different regions, and wherein the processing of the image data comprises processing data of the first quantity of ultrasound image data within the different regions.

5. A method as claimed in claim 4, wherein the processing of the image data within the different regions comprises:
   nearest neighbor interpolation;
   linear interpolation; or
   non-linear interpolation.

6. A method as claimed in claim 4, wherein the processing of the image data within the regions comprises:
   interpolation based on ultrasound signal statistics in the spatial and anatomical neighborhood.

7. A method as claimed in claim 1, wherein the processing of the image data comprises determining the location and characteristics of point scatterers and a convolution with a point spread function.

8. A tangible, non-transitory computer readable medium comprising computer executable instructions which, when said computer executable instructions are run on a computer, cause the computer to implement the method of:
   receiving low resolution image data for the anatomical regions in the form of a first quantity of ultrasound image data in respect of the anatomical regions within the volume;
   accessing a 3D model which is a representation of the anatomical regions and which defines the spatial extent of anatomy of the anatomical regions by boundaries;
   adapting the 3D model to the low resolution image data; and
   using the adapted 3D model to perform processing of the image data within each region and avoid processing together image data of different regions separated by a boundary thereby to generate a second, greater, quantity of ultrasound image data of higher resolution in respect of the anatomical regions; and
   displaying volumetric information using the second quantity of ultrasound image data at a resolution higher than that of the low resolution.

* * * * *